United States Patent

Duffy et al.

[11] Patent Number: 6,018,857
[45] Date of Patent: Feb. 1, 2000

[54] DEVICE AND METHOD FOR MOUNTING A STENT ONTO A BALLOON CATHETER

[75] Inventors: James Duffy, Trim; Geraldine Standish, Galway, both of Ireland

[73] Assignee: AVE Connaught, Galway, Ireland

[21] Appl. No.: 08/960,811

[22] Filed: Oct. 30, 1997

[51] Int. Cl.⁷ .................................................. A61M 25/16
[52] U.S. Cl. .......................... 29/407.01; 29/516; 29/282; 29/283.5; 606/95; 606/194
[58] Field of Search .................. 29/407.01, 515, 29/407.08, 282, 516, 234, 283, 235, 283.5; 606/1, 198, 194; 604/95

[56] References Cited

U.S. PATENT DOCUMENTS

| | | | |
|---|---|---|---|
| 4,699,611 | 10/1987 | Bowden | 604/51 |
| 4,830,003 | 5/1989 | Wolff et al. | 128/343 |
| 5,037,427 | 8/1991 | Harada et al. | 606/108 |
| 5,147,302 | 9/1992 | Euteneuer et al. | 604/103 |
| 5,183,085 | 2/1993 | Timmermans | 140/89 |
| 5,290,295 | 3/1994 | Querals et al. | 606/108 |
| 5,334,185 | 8/1994 | Giesy et al. | 604/164 |
| 5,344,402 | 9/1994 | Crocker | 604/96 |
| 5,352,236 | 10/1994 | Jung et al. | 606/194 |
| 5,415,664 | 5/1995 | Pinchuk | 606/108 |
| 5,425,710 | 6/1995 | Khair et al. | 604/96 |
| 5,437,083 | 8/1995 | Williams et al. | 29/235 |
| 5,496,277 | 3/1996 | Termin et al. | 604/104 |
| 5,522,882 | 6/1996 | Gaterud et al. | 623/1 |
| 5,545,210 | 8/1996 | Hess et al. | 623/1 |
| 5,546,646 | 8/1996 | Williams et al. | 29/407.08 |
| 5,569,294 | 10/1996 | Parkola | 606/194 |
| 5,575,818 | 11/1996 | Pinchuk | 623/1 |
| 5,599,352 | 2/1997 | Dinh et al. | 606/1 |
| 5,626,604 | 5/1997 | Cottone, Jr. | 606/198 |
| 5,628,754 | 5/1997 | Shevlin et al. | 606/108 |
| 5,630,830 | 5/1997 | Verbeek | 606/198 |
| 5,632,760 | 5/1997 | Sheiban et al. | 606/191 |
| 5,632,762 | 5/1997 | Myler | 606/194 |
| 5,643,278 | 7/1997 | Wijay | 606/108 |
| 5,672,169 | 9/1997 | Verbeek | 606/1 |
| 5,693,066 | 12/1997 | Rupp | 606/198 |
| 5,810,873 | 9/1998 | Morales | 606/198 |
| 5,817,100 | 10/1998 | Igaki | 606/108 |

FOREIGN PATENT DOCUMENTS

| | | |
|---|---|---|
| WO 97/09946 | 3/1997 | European Pat. Off. . |
| WO 97/23173 | 7/1997 | European Pat. Off. . |
| WO 92/15342 | 9/1992 | Japan . |

OTHER PUBLICATIONS

Boston Scientific Corporation, Scimed NIR Stent, A Medinol Ltd. Product, Instructions for Use, Rev: Jul. 1996, pp. 1–8.

Johnson & Johnson Interventional Systems Co., Directions for Use: Palmaz–Schatz balloon–expandable Stent for Coronary Arteries, 1994, 4 pages.

Global Therapeutics, Inc., Freedom Coronary Stent, Directions for Use, Jun. 1995, pp. 1–8.

*Primary Examiner*—S. Thomas Hughes
*Assistant Examiner*—Steven Blount
*Attorney, Agent, or Firm*—Sterne, Kessler, Goldstein & Fox PLLC

[57] ABSTRACT

Systems and methods for mounting a stent onto the balloon of a balloon catheter. In one embodiment, a kit is provided that includes two instruments, a first being a loader tool and a second being a profiler tool. The loader tool can be a handheld device that includes a handle at one end of the tool. A tube extends outwardly from the handle, and a wire extends is axially through the tube and projects outwardly from the tube. A balloon catheter can slide along the central wire until the balloon is delivered into the interior of the tube. A stent that is disposed about the periphery of the tube can be mounted onto the balloon by grasping the handle of the loader tool and pulling the handle and tube away from the catheter and stent whine the catheter and stent are maintained in a fixed relationship. To facilitate this mounting process, a profiler tube is included that allows a physician to provide the balloon with the proper profile to allow for, or to facilitate, the delivery of the balloon into the interior of the tube of the loader tool.

15 Claims, 3 Drawing Sheets

DEVICE AND METHOD FOR MOUNTING A STENT ONTO A BALLOON CATHETER

TECHNICAL FIELD

The invention relates to apparatus and methods for mounting an endovscular prosthesis, typically a stent, onto the balloon of a delivery catheter to enable the catheter to deliver and deploy the prosthesis within a body lumen, such as a coronary or peripheral blood vessel.

BACKGROUND OF THE INVENTION

Diseases of the vascular system afflict a substantial portion of the adult population. Many of these diseases are life-threatening conditions that demand substantial surgical intervention. For example, a stenoses or blockage of a blood vessel may develop requiring surgical intervention to open the blood vessel. Although there are traditional surgical procedures that can be effective in treating these conditions, the surgery itself can be taxing and dangerous for the patient. In particular, for many stenoses the surgical procedure requires that the patient's abdominal or chest cavity be opened to reach and expose the stenoses while it is being repaired. This is a highly invasive and dangerous surgical procedure that requires that the surgeon balance the patient's risk of harm from the disease against the patient's risk of harm from the treatment.

To reduce the mortality and morbidity resulting from these highly invasive surgical procedures, and to provide surgical treatments suitable for treating a broad range of patients, percutaneous transluminal angioplasty (PTA) and percutaneous transluminal coronary angioplasty (PTCA) techniques have been developed to reduce arterial build-up of cholesterol fats or atherosclerotic plaque. In one such procedure, a guide wire is typically maneuvered through an opening in the vascular system to the site of the stenosis. A catheter is then advanced over the guide wire through the vascular system and to the site of the stenosis. A balloon catheter is then advanced through the guide catheter so that the balloon of the balloon catheter may be property positioned within the stenosed region of the blood vessel. To alleviate the deleterious effects of the stenosis, the balloon at the distal end of the catheter is inflated to widen the blood vessel at the site of the stenosis.

Widening a blood vessel in this manner can cause flaps, fissures and dissections to form on the site of the blood vessel, which can thus cause the dilated vessel to reclose. Additionally, restenosis can occur whereby the blood vessel returns of its own accord to its original stenosed condition. To prevent reclosure or restenosis, a metal stent is typically deployed dwing the PTA or PTCA procedure to reinforce the blood vessel wall and to hold the flaps, fissures and dissections in place.

In many operations, it is necessary to deploy more than one stent during a single PTA or PTCA procedure due to the length of the stenosis in the vascular tissue. Additionally, it is often commercially advantageous to provide separately the balloon catheter and the stent so that the surgeon performing the operation can choose the appropriate stent and balloon catheter to repair the occluded blood vessel given the nature of the stenosis and the diameter of the blood vessel. Accordingly, it is frequently necessary to load a stent onto a balloon catheter prior to or during performance of the surgical procedure.

Positioning the stent on the balloon presents a number of difficulties. The balloon typically is formed from a very thin material that may be damaged if the stent is slid over the surface of the balloon during the loading procedure. This is particularly true when the stent is formed using a laser cutting procedure in which edges of the stent may be sufficiently sharp as to scratch or puncture the balloon. A scratch or puncture may increase the risk that the balloon will burst during inflation with potentially life threatening consequences to the patient. Likewise, sliding the stent with respect to the balloon may cause the stent to snag on the balloon thus deforming the stent and rendering it useless for performing PTA or PTCA.

Accordingly, it would be desirable to provide a stent mounting and transfer device for mounting a stent onto a balloon catheter which is inexpensive to manufiacture and which will reliably cause the stent to be delivered onto the balloon without damaging the balloon or deforming the stent. Additionally, it would be desirable to provide a stent mounting and transfer device which is easy and quick to use.

SUMMARY OF THE INVENTION

Accordingly, it is one object of this invention to provide a device and technique whereby a stent can be fitted onto the balloon of a delivery catheter with minimal risk of damaging the balloon and/or stent.

Another object of the invention is to provide a device and technique by which the stent can be secured in a stable position on the balloon to reduce relative movement of the stent along the balloon when the two are advanced together into and through the body lumen.

Yet another object of this invention is to provide a device for loading a stent onto a balloon catheter that is easy to manufacture and use, and that lends itself to being formed as a preassembled combination stent and loading device which can be sold as a kit.

The systems and methods described herein provide for mounting a stent or other prosthesis onto the balloon of a balloon catheter. In one embodiment, a kit is provided that includes a loader tool and a profiler tool. The loader tool can be a handheld device that includes a handle and a tube. The proximal end of the tube can couple to the handle, such that the tube projects outwardly from the handle, and provides the distal end of the tube as an opening for receiving the balloon of a balloon catheter. A wire can extend axially through the tube and project outwardly from the tube. The loader tool is dimensioned such that the central wire extending through the tube can be inserted into the guide wire lumen of a balloon catheter. The balloon catheter can slide over and along the wire until the balloon is delivered into the interior of the tube. A stent that is disposed about the periphery of the tube can be mounted onto the balloon by grasping the handle of the loader tool and pulling the handle and tube away from the catheter and stent while the catheter and stent are maintained in a fixed relationship. In this way, the tube is slid away from the stent and balloon, leaving the stent mounted about the periphery of the balloon. To facilitate this mounting process, the kit can also provides a profiler tube that allows a physician to shape the balloon with the proper profile to allow for, or to facilitate, the delivery of the balloon into the interior of the tube of the loader tool.

More specifically, a system for loading a stent onto a balloon of a balloon catheter can include a loader handle, and a loader tube having a distal end and a proximal end and being coupled to the loader handle at the proximal end. The loader tube can be dimensionally adapted to receive a balloon of the balloon catheter. A wire can be disposed within the loader tube and, optionally, project outwardly from the loader tube. The loader tube can cooperate with the wire to receive the balloon of the balloon catheter such that the balloon extends within the loader tube at least as much as a length of a stent to be delivered to the balloon.

In an optional embodiment, the loader tube comprises a substantially transparent material that can allow for a balloon that is disposed within the loader tube to be viewed through the loader tube. In one embodiment, the loader tube is comprised of a Polynimde material. Optionally, the loader tube can be formed as a cylindrical tube that has a tubular wall with a wall thickness of between approximately 0.00075 and 0.005 inches. The wall thickness of the loader tube can be selected to reduce the outer diameter of the tube and thereby facilitate providing precrimp to a prosthesis mounted about the periphery of the loader tube. Similarly, the wall thickness can be selected to be thin in order that the internal lumen that extends through the tube has a greater internal diameter. This greater internal diameter facilitates the introduction of larger diameter, or less completely wrapped, balloons.

In another embodiment, the invention can be understood as a kit for loading a stent onto a balloon of a balloon catheter. The kit can comprise a loader tool having a loader handle and a loader tube that is dimensionally adapted to receive a balloon of a balloon catheter. A wire disposed within the loader tube can extend axially and, optionally, centrally through the tube. The kit can further include a profiler tool having a profiler handle, a profiler tube coupled to the profiler handle and having a bore extending therethrough. The bore can have a tapered distal end for facilitating the insertion of the balloon into the bore. A stylet wire can be disposed within the bore and can extend axially therethrough to project outwardly from the bore. The stylet wire provides a support for the balloon catheter during insertion of the balloon into the bore. In one optional embodiment, the kit can include a stent that is disposed about the loader tube and optionally frictionally engaged therewith for reducing movement of the stent along the outer surface of the loader tube.

In another aspect, the invention can be understood as methods for loading a stent onto a balloon of a balloon catheter. The method can comprise the steps of providing a loader tool having a loader handle and a loader tube that is dimensionally adapted to receive a balloon of a balloon catheter and a central wire that is disposed within the loader tube. The method can further include mounting a stent onto the loader tube, and inserting the central wire into a guidewire lumen of the balloon catheter as well as delivering the balloon into the loader tube, and sliding the loader tube away from the stent and the balloon, while maintaining the stent and balloon in a fixed relationship. In these methods the loader tube is carried away from the stent and the balloon to leave the stent mounted onto the balloon. In an optional embodiment, the loader tube is comprised of a substantially transparent material and delivering the balloon into the loader tube includes the steps of viewing a marker on the balloon as the balloon is delivered into the loader tube to position the balloon in a selected location within the loader tube. In a further optional practice, the method includes the further steps of providing a profiler tube and profiling the balloon of the balloon catheter prior to delivery of the balloon into the loader tool.

The terms proximal and distal as used herein will be understood to describe opposite ends of a device, instrument or element, and generally will be employed so that proximal is understood as "towards the physician" and distal is understood as "away from the physician".

Other aspects and embodiments of the invention will be apparent from the following description of certain illustrative embodiments.

BRIEF DESCRIPTION OF THE FIGURES

The following figures depict certain illustrative embodiments of the invention in which like reference numerals refer to like elements. These depicted embodiments are to be understood as illustrative and not as limiting in any way.

DETAILED DESCRIPTION OF THE ILLUSTRATED EMBODIMENTS

To provide an overall understanding of the invention, the methods, systems and devices of the invention will be discussed with reference to the application of loading a stent onto a balloon catheter for performing PTCA However, it will be understood by persons of ordinary skill in the art that the general methods and devices described herein may be equally applicable to additional cases in which stents, grafts, stent-grafts or other suitable prostheses are mounted on catheters and other surgical devices, for insertion within the body. Other clinical applications of the systems and methods described herein can be made without departing from the scope of the invention.

Figure 1:
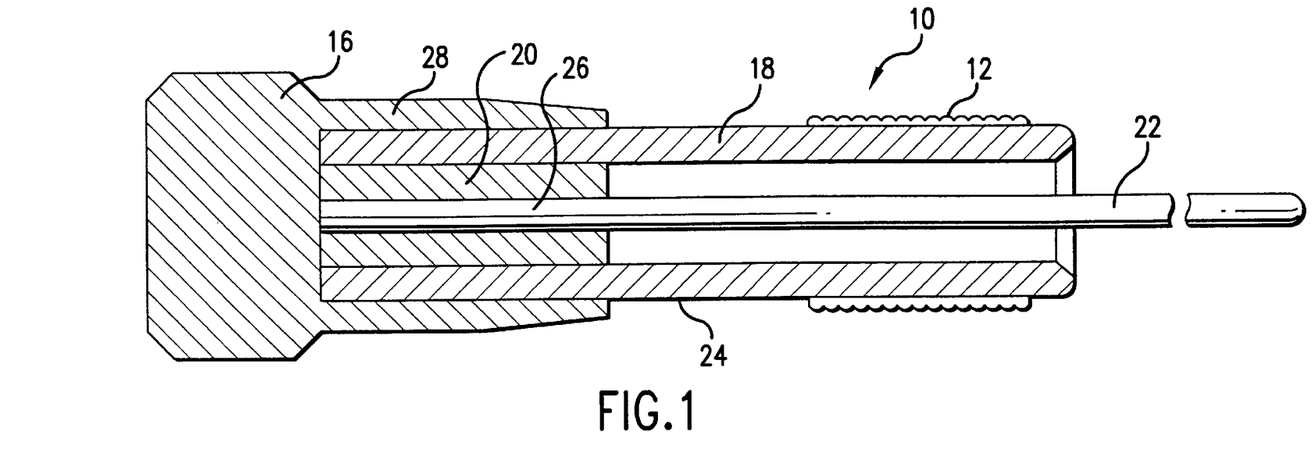
FIG. 1 depicts one embodiment of a stent loading device according to the invention.

FIG. 1 depicts one exemplary embodiment of a device for loading a stent onto the balloon of a balloon catheter. In particular, FIG. 1 depicts a loading tool 10, a stent 12, a loader handle 16, a loader tube 18, a loader head 20, and a central wire 22.

The depicted loader handle 16 can be a moulded or machined plastic handle that is about three quarters of an inch in length with a proximal circular knob that is approximately a third of an inch in diameter. The depicted handle 16 can provide a handle that allows a physician to manipulate the loader tool 10. The handle 16 can be made from plastic, including Delrin, metal or any other suitable material, and typically is made of a material that is facile to sterilize and which is relatively rigid. The handle 16 includes a sidewall 28 that extends distally from the proximal knob and is open at the distal end. The sidewall 28 defines an interior chamber dimensionally adapted to receive a stylette assembly formed from the loader head 20 and the central wire 22. The sidewall 28 can be formed of a resilient material that will yield on the insertion of the stylette assembly into the chamber and will frictionally engage with the loader head 20 to hold the loader head 20 within the chamber.

The depicted loader tube 18 may be made from any suitable material, including a Polyimide material of a semiconductor grade. Optionally, the material can be substantially transparent to allow the physician to view the balloon or a marker on a balloon of the balloon catheter during placement and alignment of the stent 12 over the balloon. However, other materials can be employed with the invention without departing from the scope thereof. The depicted loader tube is approximately 10 to 80 mm. in length, with an interior bore having an inner diameter of between about 0.05 and 0.075 inches and a sidewall thickness of approximately 0.001 to 0.005 inches. The surface of the depicted loader tube 18 can be substantially smooth to facilitate the process of sliding a stent over the tube's surfitce. Similarly, the inner surface of the depicted loader tube 18 can be substantially smooth to facilitate the process of sliding a balloon into the interior of the tube. The tube can be cylindrical, rectangular or any suitable geometry and its length can be selected to receive a portion of a balloon or the full length of one or more balloons.

The depicted loader tube 18 provides a platform onto which the stent 12 may be crimped, typically to facilitate the packaging and delivery of the stent and the loader tool. This enables the stent 12 to be packaged and shipped to the customer without damage and further ensures that the stent is ready to be mounted on a balloon of the balloon catheter. The depicted loader tube 18 has a central bore that allows wrapped balloon catheters of up to a diameter of 4.0 mm to be inserted inside the tube 18. The length of the bore can extend for the fulll length or for a portion of the tube, and for example can be 10 to 80 mm. The diameter of the central bore can vary as a function of the diameter of the wrapped balloons being inserted therein.

The illustrated central wire 22 can be approximately 170 mm in length and formed of a plastic or metal material, including AISI 304 stainless steel. The depicted central wire 22 is sized for being inserted into the guidewire lumen of a catheter and optionally can be about 2 to 14 French, or any other suitable dimension, and is typically rigid enough to support the shaft of the balloon catheter as it is being advanced into the loader tube 18. The central wire 22 also provides support to the loader tube 18 as the balloon catheter is being advanced into the bore of the tube. This support is understood to reduce the possibility of the loader tube 18 kinking and damaging the stent.

The depicted loader head 20 can have a central bore that receives the central wire 22. This may be achieved by mechanically crimping the loader head 20 onto the central wire 22. Alternative ways of joining the loader head 20 and central wire 22 include the use of suitable adhesives such as epoxy, soldering, brazing or welding, or any other method which will achieve a stable bond between these two parts. The loader head 20 can be secured within the loader handle 16 preferably by the use of an interference fit, so that the loader head 20 and central wire 22 are prevented from undergoing lateral or transverse motion relative to the loader handle 16. Alternative means of securing the loader head 20 within the loader handle 16 can optionally be employed.

The handle 16, the loader tube 18 and the central wire 22 assemble together to form the depicted loader handle 16. In the depicted embodiment these elements are held together by an interference fit that is achieved by the frictional engagement of the loader tube 18 against the sidewall 28 and the engagement of the central wire 22 within the bore of the loader head 20. The loader handle 16 has a cylindrical sidewall 28 that defines an interior chamber into which the loader head 20 and loader tube 18 can be inserted. As shown in FIG. 1, the loader head 20 and sidewall 28 engage with the loader tube 18 to hold the loader tube 18 in place. In the depicted embodiment, the loader tube 18 becomes frictionally bound between the sidewall 28 and loader head 20 once the loader tube 18 and loader head 20 are inserted into the handle 16.

FIG. 1 further depicts that central wire 22 can be inserted within a central bore that extends. through the loader head 20. As discussed above, this forms a stylette assembly that can be inserted into the chamber defined by the sidewall 28 of the handle 16. The diameter of the bore can be selected so that the central wire 22 becomes frictionally bound within the bore once inserted therein.

Although the above described embodiment employs an interference fit to bind together the elements of the loader tool, it will be appreciated that alternative techniques for coupling these parts may be employed, including adhesive bonding, set screws, and threaded parts, and further that the depicted elements can be alternatively manufactured such that two or more of the elements are integrated into a single part.

It is envisioned that the current stent loader 10 may be employed to deliver different types and sizes of stents, grafts or other suitable devices. One example of a stent which appears to be readily deployed/loaded with this device is the long bare Bard XT® stents, 24 mm and 34 mm, manufactured by C. R. Bard, Inc. of Murray Hill, New Jersey. The Bard XT® stent is a balloon expandable stent composed of multiple modules, each module consisting of a zigzag ring and connector welded to a longitudinal flexible spine. Ring and spine are made of 316 LVM stainless steel, their thickness is 0.006" or 0.15 mm. The Bard XT® stent is designed not to shorten during expansion of the rings. For each module the connector allows easy visualisation by fluoroscopy. The Bard XT stent is sterilised with EtO and is intended for single use. The stent is preferably premounted on the loading tool 10, which allows a facile, safe and accurate positioning on the delivery catheter.

Figure 2:
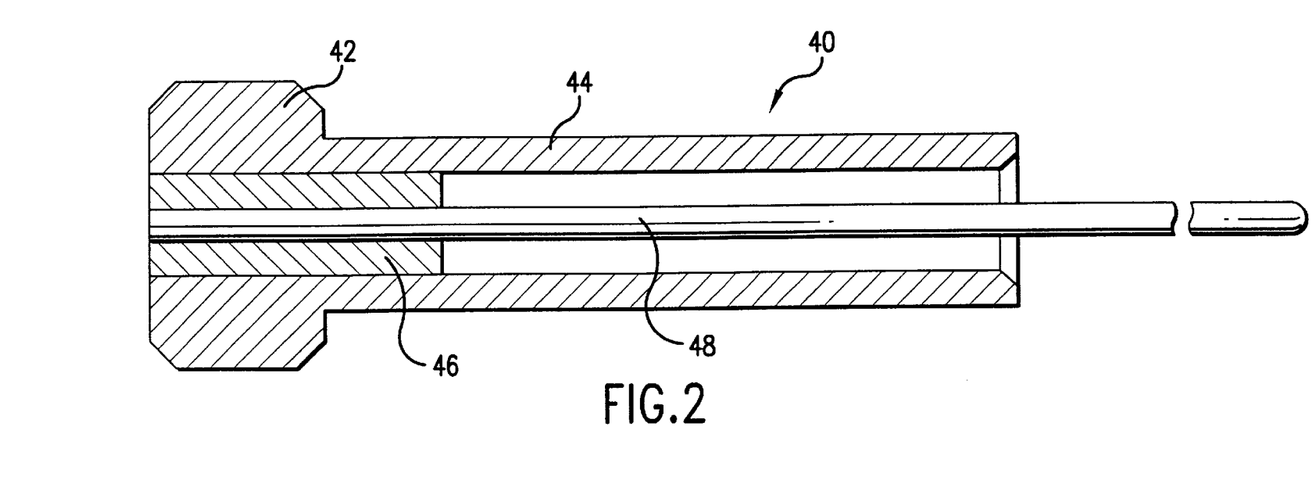
FIG. 2 depicts a device for use in profiling a balloon on a balloon catheter prior to loading the stent onto the balloon catheter.

FIG. 2 depicts a profiler tool 40 for use in packing the balloon of the balloon catheter in preparation for loading a stent onto the balloon and to facilitate entering the balloon into the tube. The depicted profile tool 40 includes a profiler handle 42, a profiler tube 44, profiler head 46 and a stylet wire 48.

The profiler handle 42 can be moulded or machined from plastic, such as Delrin, metal or any other suitable material. The profiler handle 42 can hold the parts of the profiler 40 together. This may be achieved by an interference fit between the profiler head 46 and profiler handle 42, although alternate ways of coupling these parts, such as by using adhesive, set screw, thread fitting, or other means of securing the two components in relative stationary relationship may also be employed.

The depicted profiler handle 42 is formed as a proximal knob 42 having a distally extending sidewall that forms the profiler tube 44. The profiler tube 44 can facilitate the profiling of the balloon of a balloon catheter upon insertion of the balloon into the profiler tube 44. While it is envisioned that the profiler handle 42 and profiler tube 44 can be formed of the same material and be formed as one piece in an integral manner, it would also be possible to have these two parts formed separately, and optionally, of different material.

The depicted profiler tube 44 has an interior bore extending therethrough with a diameter selected to accommodate balloon diameters up to 4.0 mm, however it should be apparent that the inner diameter of the tube 44 can be selected according to the application and the size of the balloon, or other device, being profiled. The profiler tube 44 can have a length selected to accommodate the fill length of one or more balloons, including lengths of approximately 40 mm. While Delrin is the one suitable material for forming the profiler handle 42 and profiler tube 44, it will be apparent that other material can be employed including stainless steel, glass, or any other material suitable for use in medical devices. The depicted distal end of the interior bore of the profiler tube 44 has a conical shape to provide a tapered entrance into the interior bore of the tube 44. The tapered entrance of the bore is understood to facilitate the profiling of the balloon by gradually reducing the diameter of the balloon as the balloon is delivered into bore. Other geometries, or devices for facilitating the profiling of the balloon as it is inserted into the bore can be employed without departing from the scope of the invention.

The stylet wire 48 can provide support to the balloon catheter shaft as the shaft is being advanced into the profiler tube 44. The stylet wire reduces the possibility of kinking that can result from an unsupported shaft being subjected to the resistance that can arise from the encounter between the balloon and profiler tube 44. The stylet wire 48 may be made from AISI 304 stainless steel, or any other suitable material.

The profiler head 46 retains the stylet wire 48 in a central axial disposition relative to the profiler tube 44. To that end, the depicted profiler head 46 forms an interference fit with the profiler handle 42. This interference fit prevents the profier head 46, and hence stylet wire 48, from experiencing substantial lateral or transverse relational movement with respect to the profiler handle 42. The depicted profiler head 46 can be formed from AISI stainless steel, however any suitable material can be employed without departing from the scope of the invention. The loader head 46 can be mechanically crimped onto the stylet wire 48 or joined thereto by using any suitable technique for attaching the loader head 46 to the stylet wire 48, including adhesive bonding, brazing, welding or soldering.

After the balloon of the balloon catheter has been profiled using the profiler tool 40 shown in FIG. 2, a stent can be loaded onto the balloon. Having described the loader tool 10 and profiler tool 40, a description of one process for loading a stent onto a balloon will now be described with particular reference to FIGS. 3A–3C and 4A–4E.

Optionally, the process includes the preliminary step of employing a profiler tool such as that depicted in FIG. 2 to profile the balloon of the balloon catheter. For this step the balloon typically has been prepared for delivery by flushing the guide wire lumen of the balloon catheter with heparinized saline. An inflation device is then put into fluid communication with the balloon, and a vacuum is applied to the balloon. The vacuum can be maintained during the entire loading procedure. Optimally, with the vacuum applied, the balloon should be rewrapped around its shaft to minimize the balloon profile.

Figure 3A:
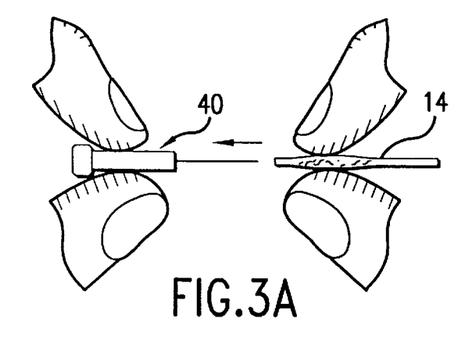
FIGS. 3A–3C depict a method of profiling a balloon on a balloon catheter using the device of FIG. 2.
Figure 3B:
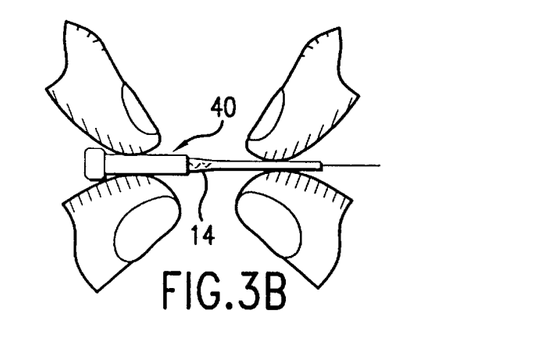
Figure 3C:
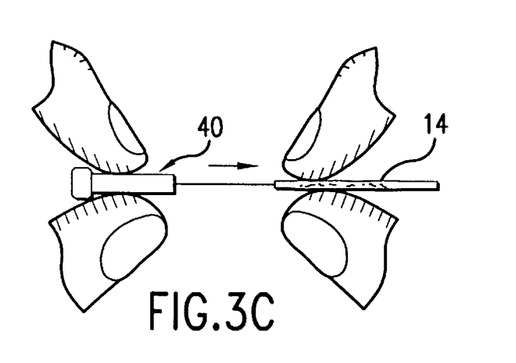

To further minimize the balloon profile, the balloon can be packed using the profiler tool 40. To this end, the stylet wire 48 of the profiler tool 40 can be inserted into a guide wire lumen of the balloon catheter as shown in FIG. 3A. Next, as shown in FIG. 3B, the balloon catheter can be advanced over the stylet wire 48 until the balloon is just contained within the profiler tool 40. In one practice, the profiler tube 44 includes a tapered distal end that causes the gradual reduction of the balloon profile as the balloon is inserted into the bore of the tube 44. The balloon can now be removed from the profiler tool 40 as shown in FIG. 3C.

Figure 4A:
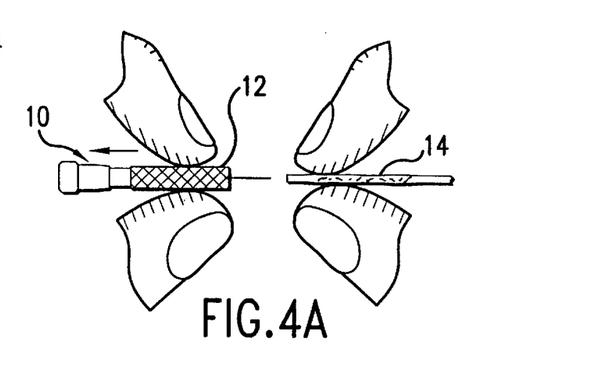
FIGS. 4A–4E depict a method of delivering a stent onto a balloon of a balloon catheter using the device of FIG. 1.
Figure 4B:
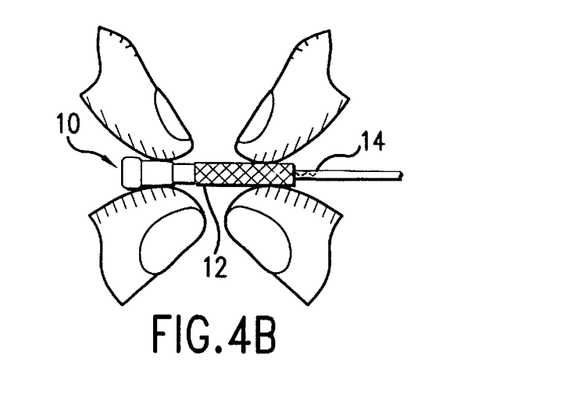

Once the balloon has been profiled, the wire 22 of the loader tool 10 can be inserted into the guidewire lumen of the balloon 14 catheter, as shown in FIG. 4A. The balloon 14 catheter is then advanced over the wire until the proximal cone of the balloon has entered into the loader tube (see FIG. 4B). At this stage, at least that portion of the balloon which is to receive the stent 12 is to be disposed within the loader tube. Optionally, the entire balloon can be inserted therein. Passage of the balloon should not be forced to avoid damage to the balloon or stent.

Figure 4C:
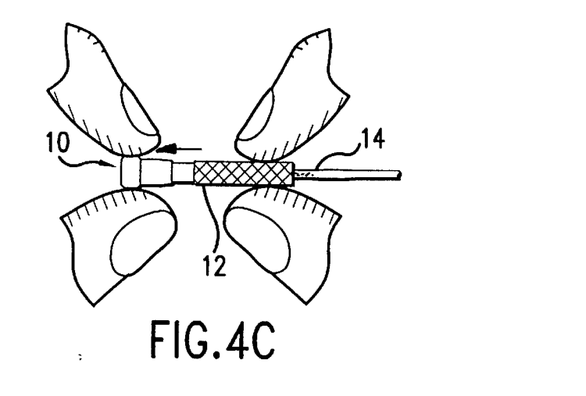
Figure 4D:
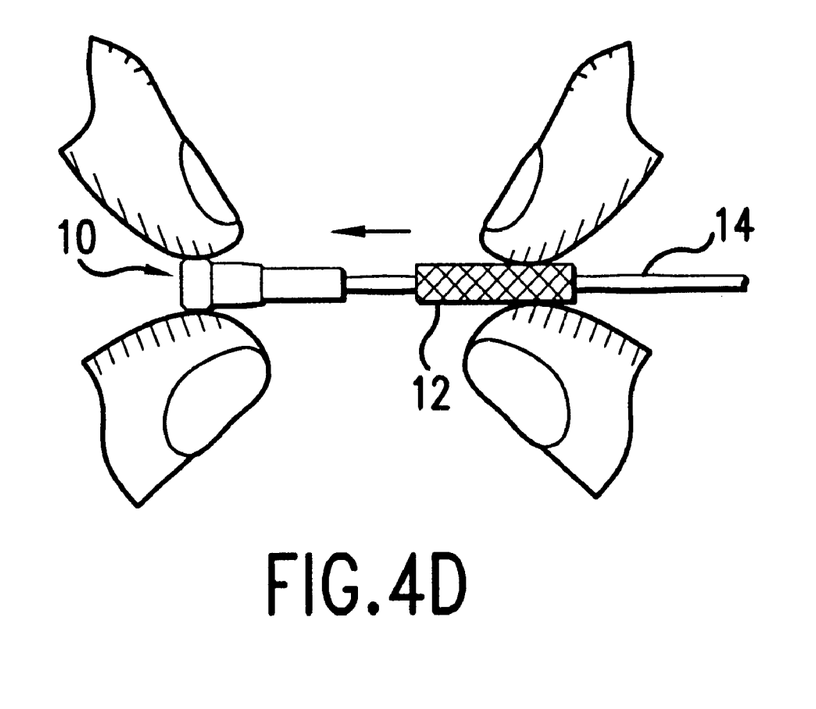

As shown in FIG. 4C, the loader tool 10 is then grasped by the loader handle 16 to hold the loader tool 10 while the stent 12 is slid along the loader tube and positioned over the balloon. Forming the loader tube of Polyimide or other transparent, or substantially transparent material, is advantageous in this process since it enables balloon markers to be visible to the physician. As a result the position of the stent 12 relative to the balloon can be judged by viewing one or more markers on the balloon, such as markers for identifying the position of the stent relative to the balloon. Excessive force should not be required to position the stent over the balloon. If excessive force is required, the stent 12 should be slid back to its original position on the loader tool 10 and the balloon should be carefully inspected to identify the cause of any abnormal resistance before continuing.

To remove the loader tool 10 from the balloon catheter, 14 the physician can use one hand to hold the stent 12 and balloon catheter 14 fixed, relative to each other, while pulling back the loader tool 10. (see FIG. 4D). In this operation, the balloon and stent can be maintained together to avoid stent displacement. Alternative methods of holding the assembly may be employed, including any suitable method that maintains the position of the stent substantially fixed relative to the balloon.

Figure 4E:
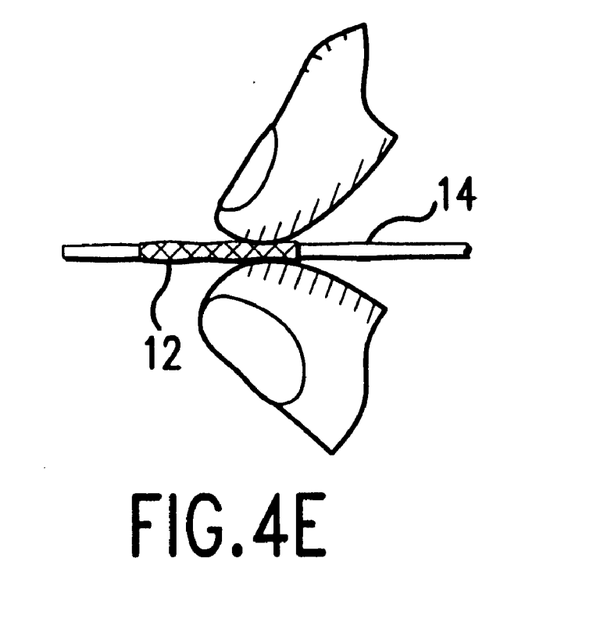

After being loaded onto the balloon, the stent 12 should be crimped, optionally over its entire length, prior to implantation, as shown in FIG. 4E. Crimping may be accomplished by starting at the center of the stent and working outwards to the ends, crimping gently between thumb and forefinger while rotating the stent and balloon. The particular method for crimping may depend on the type and size of the particular stent being loaded onto the balloon catheter. Optionally, the physician can insert a stylette or guidewire into the balloon catheter to support the shaft during the crimping process. Alternatively, as part of the operation depicted in FIG. 4D, the loader tool 10 can be pulled back far enough to clear the loader tube 18 but still leave the stylette wire 22 in the balloon catheter lumen. In this way the loader stylette wire can be used to support the balloon shaft during the crimping process.

After the stent has been crimped, the stent can be inspected to ensure that the stent has a regular appearance, and that any end modules or edges do not protrude. At this time the stent is loaded for delivery.

It will be understood that the embodiments of the invention which have been described are illustrative of some of the applications and principles of the invention. Various modifications may be made by those silled in the art without departing from the spirit and scope thereof. For example, different materials and shapes can be employed for forming the different elements of the stent loading device and balloon profiling tool. Other modifications, substitutions and additions can be made without departing from the scope of the invention. Accordingly, the invention is not to be limited to the above shown illustrated embodiments, but is to be understood by the claims set forth below, which are to be interpreted as broadly as allowed by law.

I claim:

1. A device for loading a stent onto a balloon catheter comprising:
   a loader handle;
   a loader tube made of a rigid material having a distal end and a proximal end and being coupled to the loader handle at the proximal end, the loader tube including a bore having an opening at the distal end of the loader tube extending axially through the loader tube for a distance sufficient to receive within the loader tube at least the entire portion of the balloon catheter which is to receive the stent; and a central wire disposed within the loader tube.

2. A device according to claim 1, wherein the loader tube includes a bore having an opening at the distal end of the loader tube and extending axially through the loader tube for a distance of between about 10 to 80 mm.

3. A device according to claim 1, wherein the loader tube comprise a substantially transparent material, whereby a balloon disposed within the loader tube can be viewed through the loader tube.

4. A device according to claim 1, wherein the loader tube comprises a polyimide material.

5. A device according to claim 1, wherein the central wire is dimensionally adapted to fit within a guidewire lumen of a catheter.

6. A device according to claim 1, wherein the central wire extends through the loader tube for a distance sufficient to support the catheter along the length of the catheter carrying the balloon.

7. A device according to claim 1, wherein the loader tube comprises a tubular sidewall having a wall thickness of between 0.00075 and 0.005 inches.

8. A device according to claim 1, wherein the central wire provides support to the balloon catheter lumen during a crimping process.

9. A device according to claim 1, wherein the loader tube comprises an outside dimension such that when a stent is mounted about the periphery of the loader tube, the stent will have an initial precrimp.

10. A kit for loading a stent onto a balloon of a balloon catheter, comprising:
    a loader tool having;
        a loader handle;
        a loader tube made of a rigid material having a distal end and a proximal end and being coupled to the loader handle at the proximal end, the loader tube including a bore having an opening at the distal end of the loader tube extending axially through the loader tube for a distance sufficient to receive within the loader tube at least the entire portion of the balloon catheter which is to receive the stent; and
        a central wire disposed within the loader tube; and
    a profiler tool having;
        a profler handle;
        a profiler tube made of a rigid material coupled to the profiler handle at a proximal end and having a bore extending axially through the profiler tube for a distance sufficient to receive the length of a balloon of a balloon catheter, the bore having a tapered distal end for facilitating the insertion of the balloon into the bore; and
        a stylette wire disposed within the bore and extending axially therethrough for providing a support for the balloon catheter during insertion of the balloon into the bore.

11. A kit according to claim 10, further including
    a stent disposed about the loader tube and frictionally engaged therewith for reducing movement of the stent along the loader tube.

12. A method for loading a stent onto a balloon of a balloon catheter, comprising the steps of:
    providing a loader tool having a loader handle, a loader tube made of a rigid material including a bore having an opening at the distal end of the loader tube extending axially through the loader tube for a distance sufficient to receive within the loader tube at least the entire portion of the balloon catheter which is to receive the stent, and a central wire disposed within the loader tube;
    mounting a stent onto the loader tube;
    inserting the central wire into a guidewire lumen of the balloon catheter;
    delivering said entire portion of the balloon catheter into the loader tube; and
    sliding the loader tube away from the stent and the balloon, while maintaining the stent and balloon in a fixed relationship, whereby the loader tube is carried away from the stent and the balloon to leave the stent mounted on the balloon, and thereby allow a final stent crimping to be performed.

13. A method according to claim 12, including the steps of
    providing a loader tube comprised of a substantially transparent material, and
    viewing a marker on the balloon as the balloon is delivered into the loader tube to position the balloon at a selected location within the loader tube.

14. A method according to claim 12, including the steps of
    providing a profiler tool, and
    profiling the balloon for delivery into the loader tool.

15. A device for loading a stent onto a balloon catheter comprising:
    a loader handle;
    a loader tube having a distal end and a proximal end and being coupled to the loader handle at the proximal end;
    a stent mounted onto the loader tube;
    a bore having an opening at the distal end of the loader tube extending axially through the loader tube for a distance sufficient to receive within the loader tube at least the entire portion of the balloon catheter which is to receive the stent; and
    a central wire disposed within the loader tube.

* * * * *

UNITED STATES PATENT AND TRADEMARK OFFICE
CERTIFICATE OF CORRECTION

PATENT NO. : 6,018,857  
DATED : February 1, 2000  
INVENTOR(S) : Duffy et al.

Page 1 of 2

It is certified that error appears in the above-identified patent and that said Letters Patent is hereby corrected as shown below:

In the Abstract, line 13, please delete "whine" and insert --while-- therefor;

In column 1, line 51, please delete "dwing" and insert --during-- therefor;

In column 3, line 9, please delete "Polynimde" and insert --Polyimide-- therefor;

In column 4, line 27, please insert --.-- after "PTCA";

In column 4, line 66, please delete "10" and insert --50-- therefor;

In column 5, line 4, please delete "surfitce" and insert --surface-- therefor;

In column 5, line 20, please delete "fulll" and insert --full-- therefor;

In column 6, line 60, please delete "fill" and insert --full-- therefor;

UNITED STATES PATENT AND TRADEMARK OFFICE
CERTIFICATE OF CORRECTION

PATENT NO. : 6,018,857
DATED : February 1, 2000
INVENTOR(S) : Duffy et al.

It is certified that error appears in the above-identified patent and that said Letters Patent is hereby corrected as shown below:

In column 7, line 60, please delete "balloon 14 catheter" and insert --balloon catheter 14-- therefor;

In column 7, line 61, please delete "balloon 14 catheter" and insert --balloon catheter 14-- therefor;

In column 8, line 11, please insert --12-- after "stent";

In column 8, line 16, please delete "catheter, 14" and insert --catheter 14,-- therefor;

In column 8, line 48, please delete "silled" and insert --skilled-- therefor;

In column 9, line 46, please delete "profler" and insert --profiler-- therefor.

Signed and Sealed this

Twenty-ninth Day of May, 2001

Attest:

NICHOLAS P. GODICI

*Attesting Officer*  *Acting Director of the United States Patent and Trademark Office*